United States Patent [19]

Petrofsky et al.

[11] Patent Number: 4,969,452
[45] Date of Patent: Nov. 13, 1990

[54] ORTHOSIS FOR ASSISTANCE IN WALKING

[75] Inventors: Jerrold S. Petrofsky, El Toro; Wes Piotrowski; Jannike Petrovska, both of Los Angeles, all of Calif.

[73] Assignee: Petrofsky Research, Inc., Laguna Hills, Calif.

[21] Appl. No.: 328,417

[22] Filed: Mar. 24, 1989

[51] Int. Cl.⁵ ............................................. A61F 5/02
[52] U.S. Cl. .................................. 128/78; 128/80 R; 272/70; 623/31
[58] Field of Search .................. 128/88, 80 C, 80 E, 128/80 F, 166, 83.5, 78, 80 R, 423 W, 68; 623/27, 40, 30, 32, 31; 272/70

[56] References Cited

U.S. PATENT DOCUMENTS

| | | | |
|---|---|---|---|
| 1,939,097 | 12/1933 | Bauman | 128/80 F |
| 2,362,383 | 11/1944 | Lendinara | 128/80 F |
| 2,573,866 | 11/1951 | Murphy | 23/27 |
| 2,654,365 | 10/1953 | Whitaker | 623/32 |
| 2,661,000 | 12/1953 | Gazeley et al. | 128/88 |
| 4,243,027 | 1/1981 | La Course | 128/80 F |
| 4,492,233 | 1/1985 | Petrofsky et al. | 128/421 |
| 4,531,731 | 7/1985 | Law | 272/145 |
| 4,569,352 | 2/1986 | Petrofsky et al. | 128/423 |
| 4,628,913 | 12/1986 | Lernman | 128/68 |
| 4,686,969 | 8/1987 | Scott | 128/80 C |
| 4,688,558 | 8/1987 | Hooper | 128/78 |
| 4,697,808 | 10/1987 | Larson et al. | 272/70 |
| 4,711,242 | 12/1987 | Petrofsky | 128/419 |
| 4,716,892 | 1/1988 | Brunswick | 128/80 C |
| 4,760,850 | 8/1988 | Phillips et al. | 128/432 |
| 4,796,611 | 1/1989 | Wardlaw | 128/88 |
| 4,802,466 | 2/1989 | Meyers et al. | 128/80 C |
| 4,817,588 | 4/1989 | Bledsoe | 128/80 C |

OTHER PUBLICATIONS

"Feedback Control System for Walking in Man", Petrofsky et al., Comput. Biol. Med. 14:135-139, 1984.

Primary Examiner—Robert Bahr

[57] ABSTRACT

An orthosis for assistance in walking includes a pair of flexible risers and a flexible pelvic band. Each time a leg moves forward the pelvic band is twisted and the risers are bent, thereby storing energy. At the end of the step the pelvic band and the risers tend to resume undistorted configuration, and this thrusts the opposite foot forward. An improved hip joint is also disclosed for use in combination with such risers and pelvic band. The joint has a lock plate which may be locked to a riser and also to a leg brace connected thereto.

4 Claims, 6 Drawing Sheets

ORTHOSIS FOR ASSISTANCE IN WALKING

BACKGROUND OF THE INVENTION

This invention relates to orthoses for providing assistance in walking. Such orthoses may assist persons having any of several types of walking disability, but they have particular utility for persons who have been paralyzed by a spinal cord injury. Such persons may in some cases attain walking movement by use of an appropriate orthosis. In other cases the orthosis may be used in combination with functional electrical stimulation to produce stimulated walking as described in Larson et al., U.S. Pat. No. 4,697,808.

Background information on stimulated walking is contained in Petrofsky et al. U.S. Pat. No. 4,569,352 and in a technical article entitled "Feedback Control System For Walking In Man" Petrofsky et al., COMPUT. BIOL. MED., 14:135–139, 1984. Apparatus as described in those references may use stimulation devices of the general type disclosed in Petrofsky et al. U.S. Patent 4,492,233 for stimulating muscular contractions in the lower body of the person being assisted by the system. Reference may also be made to Petrofsky U.S. Pat. 4,711,242 which discloses a control system for a knee joint incorporated within an orthosis of the general type described in Larson et al and to Phillips et al. U.S. Pat. 4,760,850 for a method of assisting the balance of a person who is being stimulated to walk.

The preferred orthosis heretofore available for use in stimulated walking has been that shown in Larson et al. That orthosis enabled considerable simplification of the stimulation system. However, the orthosis uses rigid bracing which inhibits desired body flexing. That results in a relatively jerky walking gait which causes premature fatigue of critical components of the orthosis. It also tires the user. Furthermore, it has been found that walking is difficult for a person using that orthosis on an incline, particularly uphill. This is due in part to the fact that the upper body is constrained in a rigid vertical orientation. When a normal, non-handicapped person walks up or down a hill, he leans his body forwardly or backwardly depending upon the grade. The Larson et al. orthosis will not permit such a grade adjustment.

SUMMARY OF THE INVENTION

This invention provides an improved walking assistance orthosis of the type comprising a pair of leg braces for supporting the legs of an assisted person, a pair of risers extending upwardly from the leg braces, a thoracic band for securing the upper ends of the risers to the upper body of the assisted person, and a pelvic band for interconnecting the lower ends of the riser. In one aspect of the invention the improvement resides in the fact that the risers are flexible for enabling forward and backward flexing of the upper body of the assisted person.

In another aspect of the invention the pelvic band and risers are flexible so as to store energy during forward movement of a leg and use that energy to initiate forward movement of the opposite leg. Each time a leg moves forward the pelvic band is twisted and the risers are bent, thereby storing energy. At the end of the step the band and risers tend to resume an undistorted configuration, and this thrusts the opposite leg forward.

In preferred embodiment the risers may comprise cantilevered beryllium copper inserts for providing the required flexibility. These inserts may be separated by thermoplastic spacers which may be heated and thereafter laterally contoured to the shape of the body. The pelvic band may comprise a stress-free molded graphite and fiberglass cloth laminate or other flexible material having similar properties.

The orthosis of this invention also has an improved joint between the riser and the leg brace. This joint has a lock plate which may be locked to the leg brace and also to the riser. There is a first lock means which locks the lock plate, preferably to the leg brace, to provide vertical support during standing and walking. A second lock means preferably locks the lock plate to the riser in a selected one of a plurality of relative positions thereby adjusting the stance angle of the standing position and hence the center of gravity of the body for balance. About plus or minus 15 degrees of adjustment may be provided.

It is therefore an object of this invention to provide an orthosis for stimulated walking which provides required body support while enabling flexing to accommodate postural adjustment and provide efficient energy transfer.

Other and further objects of the invention will be apparent from the following description, the accompanying drawings and the appended claims.

DESCRIPTION OF THE PREFERRED EMBODIMENT

Figure 1:
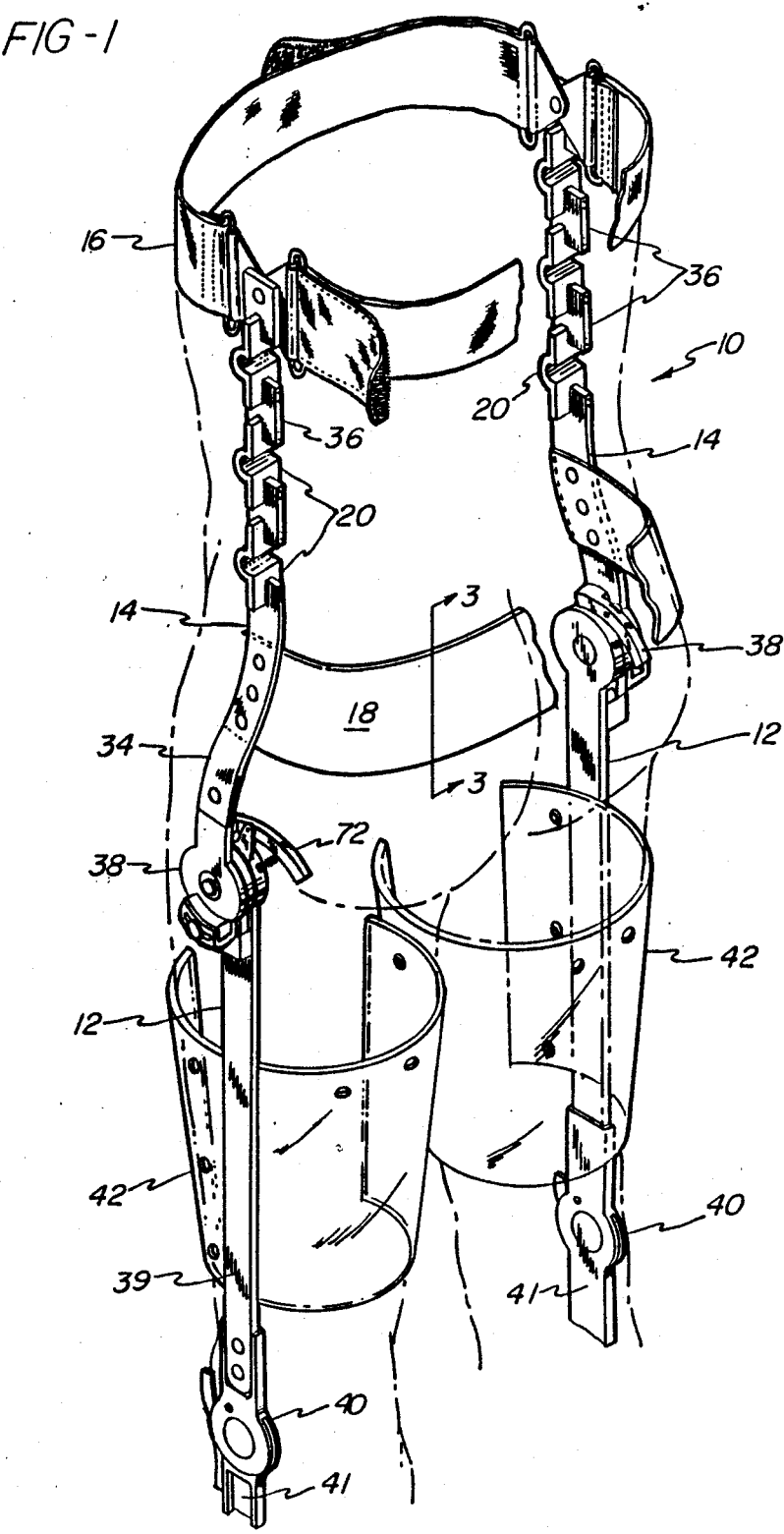
FIG. 1 is a perspective view of an orthosis for stimulated walking in accordance with this invention.

An orthosis 10 in accordance with the present invention may be attached to the body of a handicapped person as generally illustrated in FIG. 1. Orthosis 10 comprises a pair of leg braces 12,12 attached by means of a pair of hip joints 38,38 to a pair of risers 14,14. Risers 14,14 are secured to the upper body of the wearer by a thoracic band 16. The lower ends of risers 14,14 are interconnected by a pelvic band 18 which is custom made for the wearer as hereinafter described.

Figure 2:
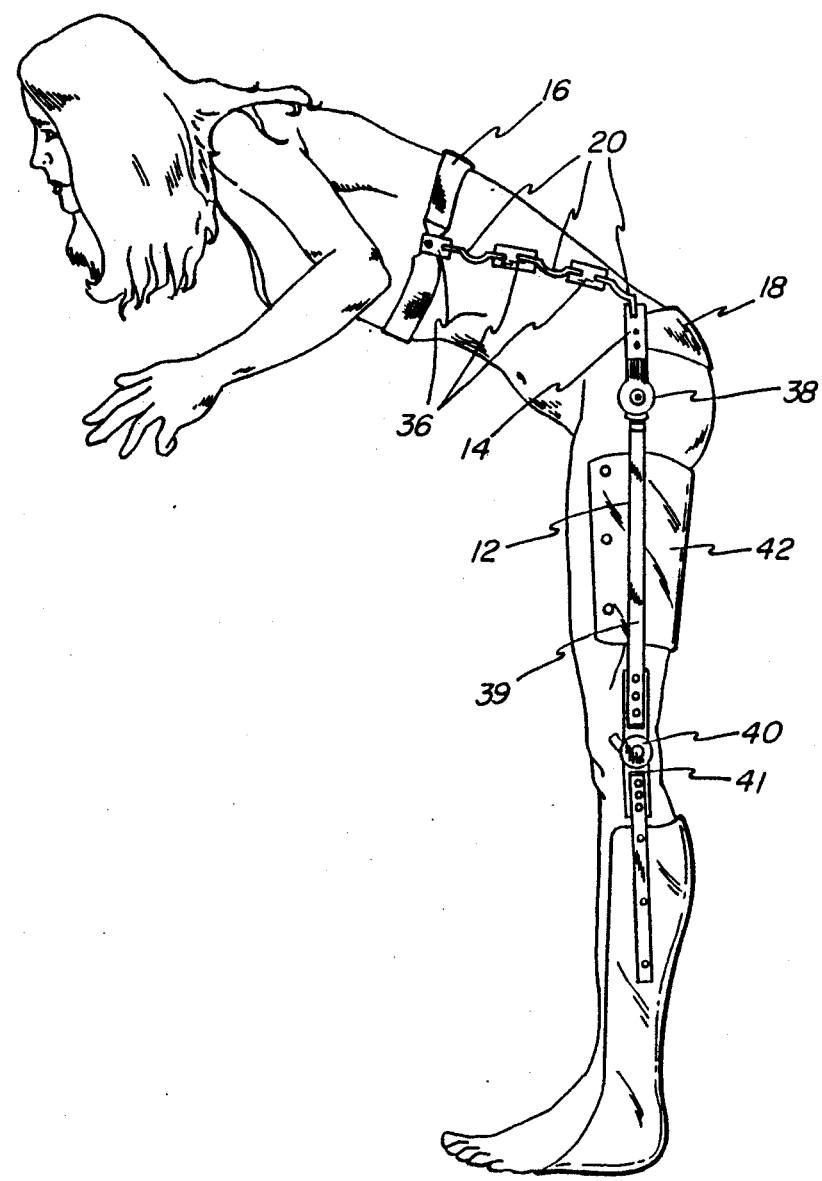
FIG. 2 is a schematic drawing of forward flexing by a person wearing the orthosis of FIG. 1.

Leg braces 12 may be of conventional design. Accordingly, each leg brace 12 may comprise an upper support rod 39 pivotally attached to a lower support rod 41 by means of a gravity-lock knee joint 40. Alternatively, a bail lock knee joint may be used. Foot supports 43,43 (FIG. 2) may be secured to the lower ends of lower support rods 41,41. A pair of thigh clamps 42,42 may be mounted on upper support rods 39,39 for gripping the thighs of the wearer. Thigh clamps 42,42 are preferably constructed of flexible plastic and may be secured to the legs by straps of the hook and loop fabric type (not illustrated).

It has been found that risers 14,14 should have a flexibility inversely related to the weight of the wearer. As the wearer bends over, risers 14,14 should generate restoring torques which balance the body weight. The riser flexibility should be selected in accordance with body weight. Assuming that ¾ of the weight is located above the hip joint and the center of gravity above the hips is ⅜ of the height from the hips to the top of the head, the total torque of the riser must be Total Torque =

$$[0.75 \text{ (body weight)}] [⅜(\text{body height} - \text{height of hips})]$$

Torque on each riser = Total Torque/2 e.g. for a 100 lb. woman who is 70" tall with hip height of 30", $$\text{Total Torque} = (.75)(100) \left[ (⅜) \frac{(70 - 30)}{12''} \right]$$

$$= (75)(⅜) \quad 170 \text{ foot lbs. or 85 foot lbs./riser}$$

This amount of torque will only be present when the body is bent over. Smaller movements will produce less restoring torque. In a typical case, risers 14,14 may generate a total restoring torque of approximately 40 ft. lbs. when the body bends forward 1 inch.

In the preferred embodiment as illustrated in FIG. 1, riser flexibility is provided by beryllium copper inserts 20. For a female of average height and weight, each riser 14 may comprise 3 beryllium copper inserts 20 approximately 0.025 inches thick, ¼ inch wide and cantilevered about a C-shaped bend of about ¾ inch diameter. If the wearer bends all the way over to touch toes, these inserts will generate a restoring torque of approximately 80 ft.-lbs. each. A heavier person might be provided with inserts having a thickness of about 0.030 in which case a full forward body bend would generate approximately 180 ft.-lbs. of restoring torque in each riser. For a very lightweight person, the inserts may be only about 0.020 inches thick for generating a maximum restoring force of about 40 ft.-lbs.

It will be observed that risers 14,14 may also be flexed rearwardly, but the human body anatomy restricts such rearward flexing to a relatively small angle. All such balanced forward and rearward flexing is performed with hip joints 38,38 locked to maintain leg braces 12,12 in generally collinear relationship with the lower ends of risers 14,14. Hip joints 38,38 are also locked during stimulated walking and are unlocked during sitting, as hereinafter described.

While inserts 20 permit balanced forward and rearward body flexing, sideward flexing is substantially resisted. At the same time, however, risers 14,14 should be sidewardly shaped to follow the contour of the body. Such shaping is provided by spacers 36 and riser shanks 34,34. Spacers 36 and riser shanks 34,34 are fabricated from a thermoplastic material such a polypropolene. These elements are heated and shaped to the body of the wearer as a step in the manufacturing process.

When risers 14,14 are constructed as above described, the wearer is able to tilt his body forwardly or rearwardly as necessary to accommodate an incline during stimulated walking. As noted above, stimulated walking is accomplished with hip joints 38,38 locked. This causes alternating twisting of pelvic band 18 accompanied by bending of risers 14,14. Pelvic band 18 is constructed of a material which is sufficiently flexible to accommodate such twisting and sufficiently stiff to transfer energy back and forth from leg to leg during walking. Maximum twist occurs at the end of a step with the legs farthest apart. The energy which is stored in the pelvic band by virtue of this twist causes an untwisting motion which pulls the rearward leg forward. Minimum twisting occurs at mid-step with the legs side-by-side. As the leg which had been rearward continues forward, it imparts a reverse twist on pelvic band 18, thereby storing energy to initiate forward movement of the opposite leg at the beginning of the next step.

It has been found that pelvic band 18 performs well when constructed of resin impregnated graphite and fiberglass cloth. Thermoplastic graphite cloth laminates are commercially available, but these laminates have been found to be unsatisfactory for the present purpose. When such laminates are heated and then deformed, they develop stresses which tend to cause relaxation of the shape over a period of time. These stresses also cause a delamination tendency. For these reasons it is desirable to vacuum laminate the structure to the shape of the wearer.

The production of a pelvic band 18 preferably commences with producing a positive plaster casting of the lower back region of the user. This may be done by conventional casting techniques.

After the plaster casting is available, it is covered with a cloth stockinette. The cloth stockinette is covered with a piece of graphite and fiberglass cloth, and this is covered at the ends only with small pieces of fiberglass cloth. The entire assembly is then covered by a second stockinette and thereafter perforated at the ends for reception of attachment rings (see ring 30 of FIG. 4). Attachment rings are then inserted, and the structure is ready for resin impregnation.

Figure 3:
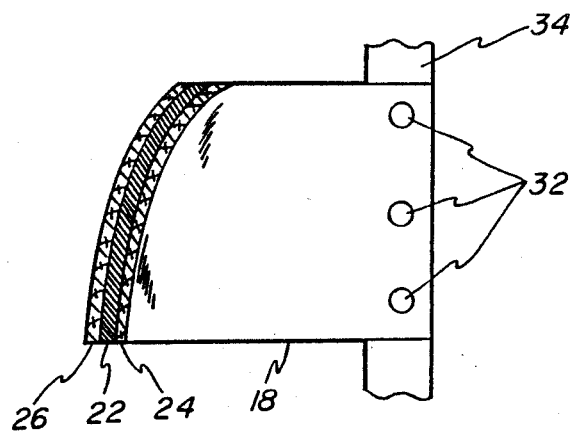
FIG. 3 is a cross-sectional drawing of a pelvic band.
Figure 4:
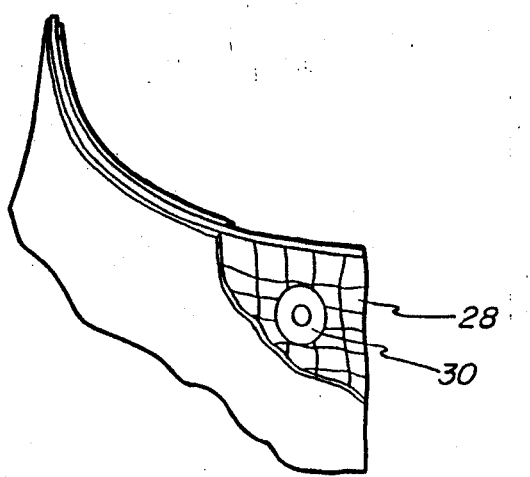
FIG. 4 is a cut-away drawing of a pelvic band illustrating the mounting of an attachment ring.

After the above series of steps have been performed, the positive plaster casting with the above described assembly thereon is placed in an acetate bag which has been soaked with alcohol. An acrylic resin mixture is prepared and poured into the bag. A vacuum is then applied for about 5 minutes as the plastic is needed over the cloth. This produces a stress-free molded graphite cloth laminate suitable for practicing this invention. The laminate is trimmed with a saw and attached to riser shanks 34,34 by means of rivets 32 (FIG. 3) which are passed through attachment rings 30. As illustrated in FIGS. 3 and 4, the final structure of pelvic band 18 comprises stockinette layers 24,26 with a graphite cloth sheet sandwiched therebetween. A fiberglass cloth section 28 provides reinforcement at the ends.

A pelvic band constructed as described above has been found suitable for use by persons of slender and normal build. A heavy, muscular person might require more stiffness in the pelvic band. If so, a second graphite cloth layer may be included in the lamination.

A working example of a pelvic band produced as above described uses the following components:

Cloth Stockinette
Nylon Krausel sold under
tradename "Otto Bock", obtained from
Kingsley Mgf. Co. of Costa Mesa, California
under Catalogue No. 623T8
Fiberglass Matting
Kingsley Mfg. Co., -continued Catalogue No. 61664
Graphite Cloth
warp yarn: graphite 12 K + E-Glass
fill yarn: E-Glass
wt: 11.39 oz/sq. yd.
thickness: 0.023 in.
manufacturer: Textile
Technologies, Inc.
style: U 111
Acrylic Resin
Orthocryl TM 80:20
lamination resin (Catalog
Order 617H20) with 32 BZP
catalyst, 20 PROM
Diethylaniline promoter and
617P37 Hardener Powder (all
available from Kingsley Mfg.
Co.)

Locking of hip joints 38,38 is provided by a releasible locking arm 72. As illustrated in detail in FIGS. 5–7, locking arm 72 comprises a finger 73 which engages a locking recess 70 in lock plate 67. A mounting pin 75 mounts locking arm 72 on a shoulder 71 of the head 68 of upper support rod 39. A compression spring 74 urges locking arm 72 into locking engagement with lock plate 67. When the wearer wishes to sit down, he depresses the distal end 78 of locking arm 72 to disengage the locking mechanism. He then bends forward slightly, so that lock finger 73 rides up on the outer surface of lock plate 67 to enable unrestricted rotation of hip joint 38.

Lock plate 70 is sandwiched between two washers 65,66, which in turn are sandwiched between the foot 54 of riser 14 and the head 68 of upper support rod 39. The entire assembly is fastened together by bolts 76 and lock washers 77.

Figure 5:
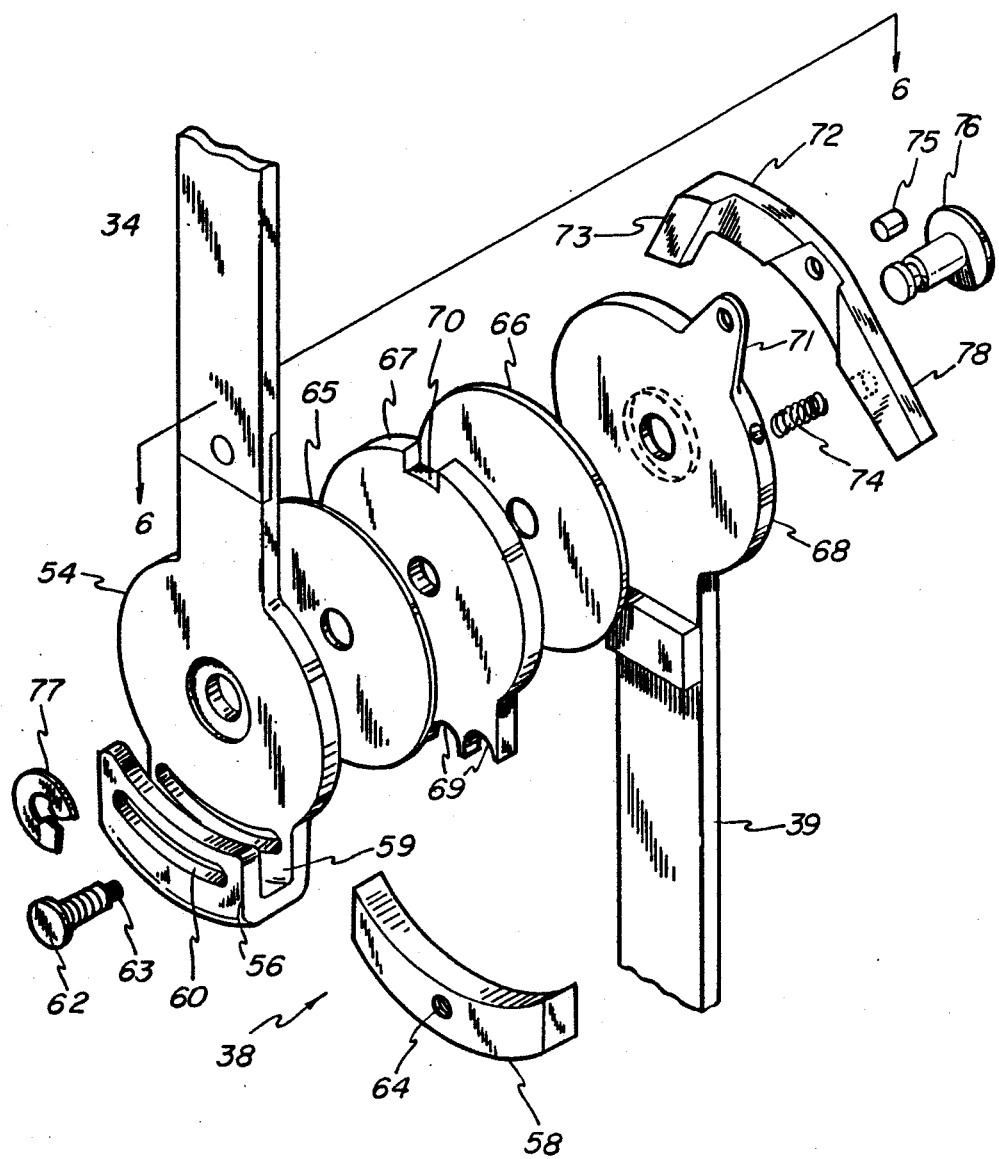
FIG. 5 is an exploded perspective view of a hip joint.
Figure 6:
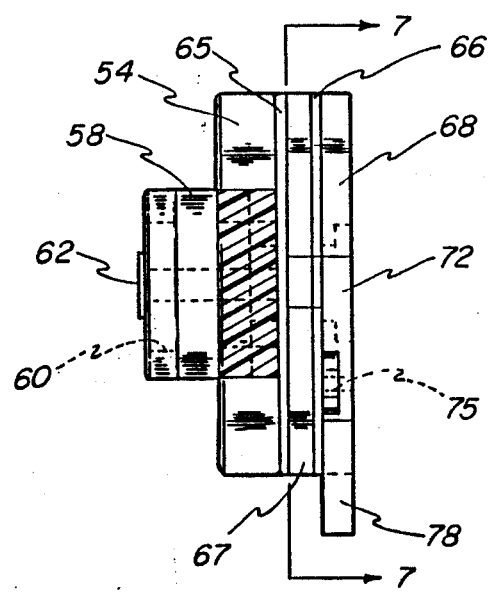
FIG. 6 is a top plan view of the hip joint of FIG. 5.
Figure 7:
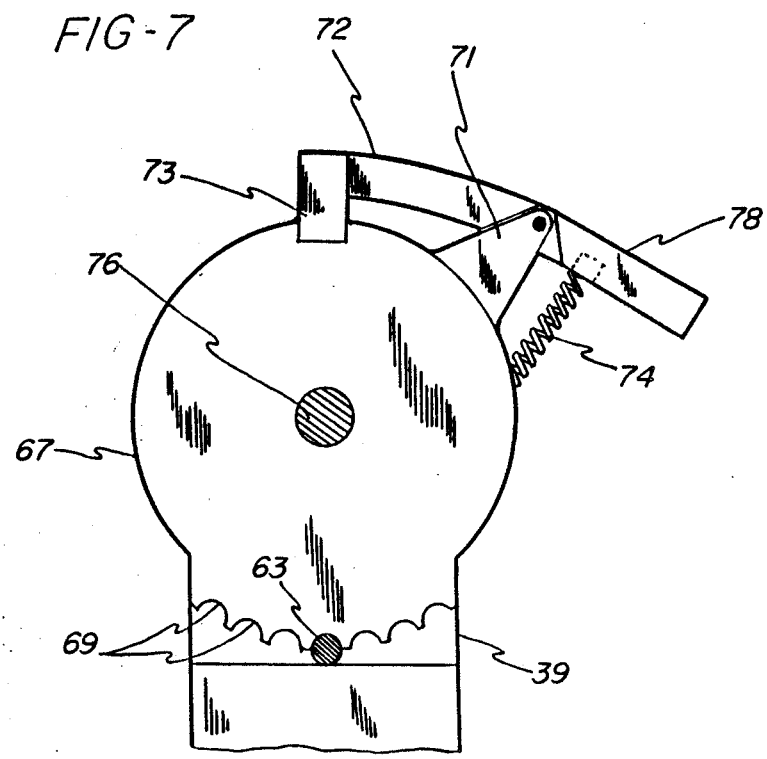
FIG. 7 is a cross-sectional view of a hip joint taken along line 7—7 of FIG. 6.

It has been found that while leg braces 12 should be nominally collinear with risers 14 during stimulated walking, some adjusting of the angular relationship therebetween is desirable in order to accommodate postural variations among individuals. Thus lock plate 67 is provided with a series of grooves 69 which enable fixed, minor variations in the nominal locking angle. The arrangement as illustrated in FIGS. 5–7 permits leg braces 12 and riser 14 to be locked in a relationship which varies as much as plus of minus 15 degrees from collinear. The amount of the adjustment is controlled by inserting the smooth end 63 of a threaded bolt 62 through arcuate slot 61 in riser foot 54 and into engagement with one of the grooves 69.

Riser foot 54 has an upturned flange 56 which defines a channel 59. An arcuate shoe 58 is fitted into channel 59. Bolt 62 passes through an arcuate slot 60 and upturned flange 56 and is threaded into a threaded passage 64 in shoe 58. This locks the head of bolt 62 against flange 56, thereby preventing rotation of lock plate 67.

Figure 8:
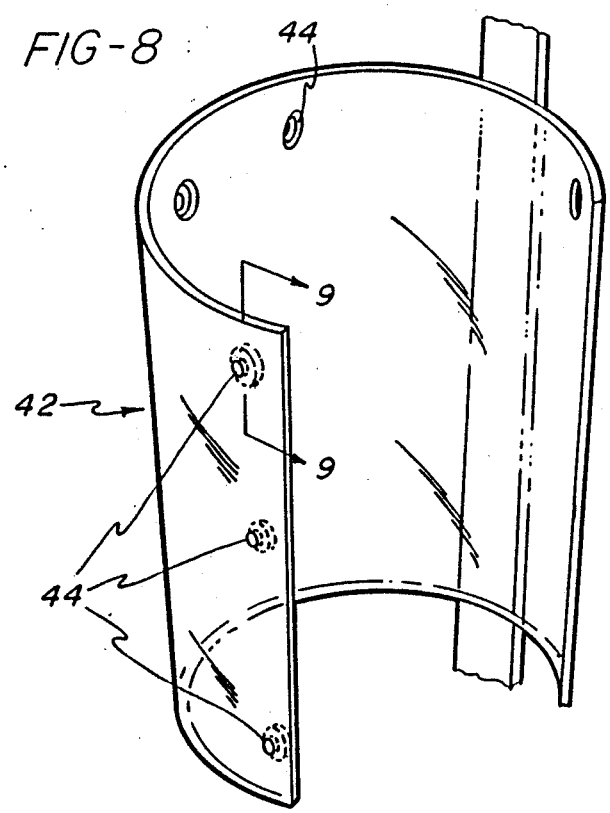
FIG. 8 is a perspective view of a thigh clamp.
Figure 9:
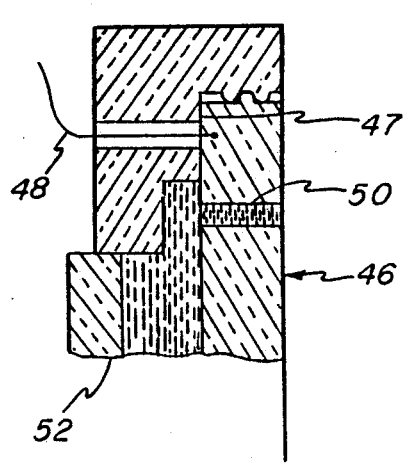
FIG. 9 is an enlarged cross-sectional view of a stimulation electrode installation in a thigh clamp, taken along line 9—9 at FIG. 8.
Figure 10:
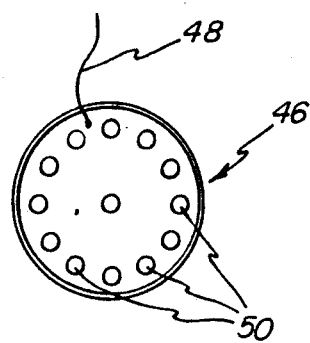
FIG. 10 is a plan view of a stimulation electrode.

As illustrated in FIGS. 8 and 9, a thigh clamp 42 may be provided with a series of electrode passages 44. Conductive plastic electrodes 46 (see FIG. 10) are inserted into recesses 47 in passages 44 so as to be in contact with the skin of the wearer. An electrically conductive gel is squeezed into each passage 44 and is extruded through openings 50 in electrodes 46. This produces good electrical contact with the skin of the wearer. Electrical connection is completed by means of a lead wire 48. Electrode passages 44 may be closed with plugs 52.

Lead wires 48 of thigh clamps 42,42 may be connected t pulse generators and stimulation driving as illustrated in FIGS. 11 and 12 of Larson et al. 4,697,808. This provides for stimulation of the quadriceps and hamstring muscle groups. Other electrodes may be sewn into an appropriate undergarment for stimulation of the gluteus maximus muscles.

While the form of apparatus herein described constitutes a preferred embodiment of this invention, it is to be understood that the invention is not limited to this precise form of apparatus, and that changes may be made therein without departing from the scope of the invention which is defined in the appended claims.

What is claimed is:

1. Orthosis for simulated walking comprising a pair of leg braces having upper ends and being configured for supporting the legs of an assisted person, a thoracid band for attachment to the upper body of said person, a pair of risers having lower ends secured to the upper ends of said leg braces and upper ends secured to said thoracic band, and a pelvic band shaped to fit around the body of said person and interconnect the lower ends of said risers; characterized in that said risers comprise flexing means intermediate the lower and upper ends thereof, said flexing means having sufficient flexibility to enable bending of the upper body of said person and sufficient flexing resistance to react to said bending by generating a restoring torque to support the upper body weight of said person and assist in recovering a vertical stance.

2. An orthosis according to claim 1 characterized in that said pelvic band is constructed of a material which is sufficiently flexible to twist during walking movement by said person and yet is sufficiently stiff to react to maximum twisting by generating an untwisting motion having enough energy to pull a rearward leg forward.

3. An orthosis according to claim 1 characterized in that said riser flexing means comprises a plurality of cantilevered beryllium copper inserts.

4. An orthosis according to claim 3 characterized in that said pelvic band comprises a "stress-free" molded graphite cloth laminate for storing energy during forward movement of a leg and using said energy to initiate forward movement of the opposite leg.

* * * * *